United States Patent
Rodriguez et al.

(10) Patent No.: US 10,729,344 B2
(45) Date of Patent: Aug. 4, 2020

(54) SYSTEMS AND METHODS FOR MEASURING CARDIAC TIMING FROM A BALLISTOCARDIOGRAM

(71) Applicant: THE REGENTS OF THE UNIVERSITY OF CALIFORNIA, Oakland, CA (US)

(72) Inventors: Cameron Rodriguez, Santa Monica, CA (US); Mark S. Cohen, Santa Monica, CA (US); Agatha Lenartowicz, Pasadena, CA (US)

(73) Assignee: The Regents of the University of California, Oakland, CA (US)

( * ) Notice: Subject to any disclaimer, the term of this patent is extended or adjusted under 35 U.S.C. 154(b) by 524 days.

(21) Appl. No.: 15/355,302

(22) Filed: Nov. 18, 2016

(65) Prior Publication Data

US 2017/0065196 A1    Mar. 9, 2017

Related U.S. Application Data

(63) Continuation of application No. PCT/US2015/031843, filed on May 20, 2015.

(Continued)

(51) Int. Cl.
*A61B 5/0476* (2006.01)
*A61B 5/04* (2006.01)
(Continued)

(52) U.S. Cl.
CPC ...... *A61B 5/04012* (2013.01); *A61B 5/04028* (2013.01); *A61B 5/0476* (2013.01);
(Continued)

(58) Field of Classification Search
CPC . A61B 5/04012; A61B 5/0478; A61B 5/1102; A61B 5/7203
See application file for complete search history.

(56) References Cited

U.S. PATENT DOCUMENTS

| 2007/0233192 | A1 | 10/2007 | Craig |
| 2008/0262367 | A1* | 10/2008 | Mugler ............... A61B 5/0452 600/523 |

FOREIGN PATENT DOCUMENTS

| KR | 10-0866547 B1 | 11/2008 |
| KR | 10-1238192 B1 | 2/2013 |

(Continued)

OTHER PUBLICATIONS

Korean Intellectual Property Office (KIPO), International Search Report and Written Opinion, dated Sep. 8, 2015, related PCT international application No. PCT/US2015/031843, pp. 1-11, with claims searched, pp. 12-17. The relevance of non-English language references WO 2011/132756, KR 10-0866547, and KR 10-1238192 is indicated therein.

*Primary Examiner* — Puya Agahi
(74) *Attorney, Agent, or Firm* — Quarles & Brady LLP

(57) ABSTRACT

A system and method to extract the timing of ECG events without reliance on ECG. The system and method are based on effects of scalp pulsation (due to blood flow) on electrode location. The electrodes in the system with the closest proximity to the facial arteries are re-referenced to create a [Mean Left-Mean Right] signal (LRM). A constrained peak detection algorithm is then used to find the BCG events. Finally, an automatic error checking and correction algorithm based on inter-beat timing is applied.

10 Claims, 9 Drawing Sheets

Related U.S. Application Data

(60) Provisional application No. 62/000,924, filed on May 20, 2014.

(51) Int. Cl.
*A61B 5/0402* (2006.01)
*A61B 5/0478* (2006.01)
*A61B 5/11* (2006.01)
*A61B 5/00* (2006.01)

(52) U.S. Cl.
CPC .......... *A61B 5/0478* (2013.01); *A61B 5/1102* (2013.01); *A61B 5/7203* (2013.01)

(56) References Cited

FOREIGN PATENT DOCUMENTS

| WO | 2011-132756 A1 | 10/2007 |
| WO | 2012-107843 A2 | 8/2012 |

* cited by examiner

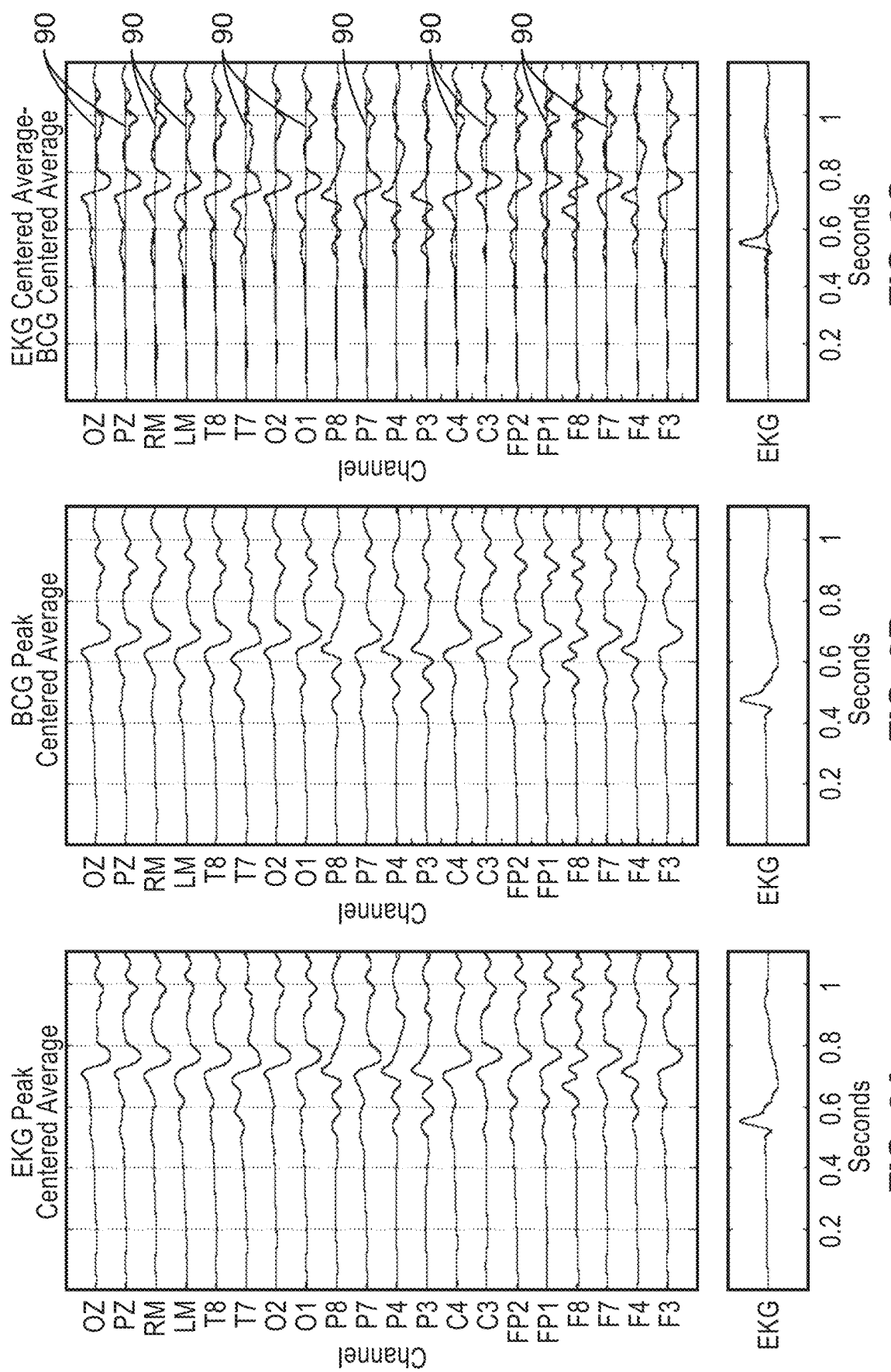

SYSTEMS AND METHODS FOR MEASURING CARDIAC TIMING FROM A BALLISTOCARDIOGRAM

CROSS-REFERENCE TO RELATED APPLICATIONS

This application is a 35 U.S.C. § 111(a) continuation of PCT international application number PCT/US2015/031843 filed on May 20, 2015, incorporated herein by reference in its entirety, which claims priority to, and the benefit of, U.S. provisional patent application Ser. No. 62/000,924 filed on May 20, 2014, incorporated herein by reference in its entirety. Priority is claimed to each of the foregoing applications.

The above-referenced PCT international application was published as PCT International Publication No. WO 2015/179567 on Nov. 26, 2015, which publication is incorporated herein by reference in its entirety.

STATEMENT REGARDING FEDERALLY SPONSORED RESEARCHER DEVELOPMENT

Not Applicable

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

This description pertains generally to neurology, and more particularly to electrocardiogram (ECG) signal processing.

2. Background Discussion

Electroencephalography, or EEG, is the recording of electrical activity from the scalp. EEG measures voltage fluctuations that result from ionic current flows within the brain. In clinical contexts, EEG is recorded from multiple electrodes placed on the scalp for periods of minutes to days. Diagnostic applications include detection of normal and abnormal markers of brain function such as observations of brief or extended electrical events that are pathognomonic of certain diseases or of brain and cognitive states. In the clinic, the EEG plays important roles in sleep medicine, epilepsy, brain tumors, anesthesia monitoring, coma, and other serious medical conditions. The analysis of the EEG often includes evaluation of its spectral content of EEG, referring to the common presence of oscillatory components to these signals.

Ballistocardiogram Artifact (BCG) refers to contaminate signals in an electroencephalogram that arise from movement of the body, blood and electric charge across blood vessels due to heart pulsation, particularly when the EEG is recorded within a magnetic field, such as is encountered in a Magnetic Resonance Imaging (MRI) environment.

Electrocardiography (EKG or ECG) is a measure of the heart's electrical activity. Hereafter, the single designation ECG will be used to refer to this signal. ECG is typically a transthoracic (across the thorax or chest) interpretation of the electrical activity of the heart over a period of time, as detected by electrodes attached to the surface of the skin and recorded by a device external to the body. It picks up electrical impulses generated by the polarization and depolarization of cardiac tissue and translates into a waveform. The waveform is then used to measure the timing of heartbeats. The recording produced by this noninvasive procedure is termed an electrocardiogram (ECG).

Under a variety of circumstances, and particularly when EEG signals are acquired during magnetic resonance imaging, the BCG (and at times the ECG) can contaminate the desired EEG signals.

Several methods exist to suppress these artifactual contaminations, but these, in general, depend on accurate timing information for the cardiac-related BCG and ECG signals. Poor quality of the ECG recording will contribute to errors that can occur easily from incorrect placement of the electrodes and/or poor synchronization of the EEG and ECG recordings.

There have been attempts to extract cardiac timing from the BCG. These methods have generally used the mean of the rectified/absolute signal (often referred to as the global field power (GFP)) to emphasize the BCG artifact and extract its timing. However the variance between the timing in this method and the measured cardiac timing often is excessive, leading to poor artifact suppression. As such, the current state of the art for measuring the timing of the BCG events is to infer it based upon the timing of the R-wave complexes of a simultaneously recorded ECG. Where the ECG signal arises from a single source, the change in polarization of the heart muscle, the BCG artifact arises from multiple sources only one of which has a tight time lock to the heartbeat. As a result of the multiple sources of the BCG artifact, there is discrepancy in the timing between ECG signals and some of the components of the BCG artifact. This leads ultimately to poor artifact rejection and degraded EEG.

BRIEF SUMMARY

In one aspect of the disclosure, a system is disclosed for measuring the timing of the BCG directly from the EEG recordings, in order to eliminate the most important sources of error that stem from the ECG recording. This improves the ability of the system to remove the contaminating BCG from the EEG recording.

Another aspect is a system and method to extract the timing of electrocardiographic events without reliance on ECG. The system and method are based on effects of scalp pulsation (due to blood flow) on electrode location. Unlike the other two sources of BCG (cardiac induced head movement and the Hall effect from the motion of the blood in the magnetic field) the timing of the hydromechanical coupling/lag to the cardiac cycle to the blood vessel pulsation is locked tightly. The electrodes in the EEG system with the closest proximity to the facial arteries are re-referenced to create a [Left Mean-Right Mean] signal (LRM). A peak detection algorithm is then used to find the timing of the BCG events in the LRM signal. This timing can then be used in a BCG cleaning algorithm of choice or used to seed additional peak detection within individual EEG channels the timing of which can then be fed into a BCG cleaning algorithm of choice.

The systems and method of the present description are more accurate in finding BCG events as compared to using the ECG signal, as the present system and method find the events themselves rather than inferring them from a correlated but not locked signal. The LRM also is more reliable and accurate than using an alternate, global field power (i.e., mean of the absolute signal, MAS), approach, as the GFP draws its signals from all electrodes rather than those lying directly above the arteries. This causes the GFP signal to have heavier weight in BCG components as compared to the LRM from both head movement and the Hall effect.

Further aspects of the technology will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

FIG. 8A through FIG. 8C are plots illustrating windowing about the various detected peaks for numerous EEG channels and for the ECG.

DETAILED DESCRIPTION

One realization of the present disclosure is based on the observation that second to the gradient artifact, the ballistocardiogram artifact (BCG) typically is the largest contaminant of electroencephalographic (EEG) recordings acquired within the Magnetic Resonance Imaging (MRI) environment. The strength of the BCG artifact contamination in a typical 3 Tesla MRI system is on the order of 10 times greater than the EEG signal itself. Making matters worse, this ratio scales with magnetic field strength.

The BCG artifact is believed to originate from three main sources: displacement of the electrodes from scalp movement, rotation and translations of the head from cardiac movements, and the Hall effect from the motion of the blood in the magnetic field. Each contamination source generates a voltage difference between the electrodes that contributes to the ballistocardiogram.

Existing algorithms that deal with this issue use a variety of means to estimate the waveform of the BCG and to subtract it from the contaminated signal. Generally, this entails various forms of windowing the EEG recording about the cardiac cycle, the timing for which typically is obtained from simultaneously recorded electrocardiogram (ECG).

The ECG recording itself is a source of errors when used with current standard cleaning algorithms.

First and foremost, using the ECG to window/clean the BCG artifact assumes that the two events are time-locked. While correlated, this time locking is neither guaranteed nor reliable. The variability comes from the dynamics of the coupling between electrical signaling of the heart and the multiple of source of the BCG signal. It is the lack of time lock between the ECG and all of the BCG components that leads to suboptimal cleaning from ECG based time points.

Figure 3:
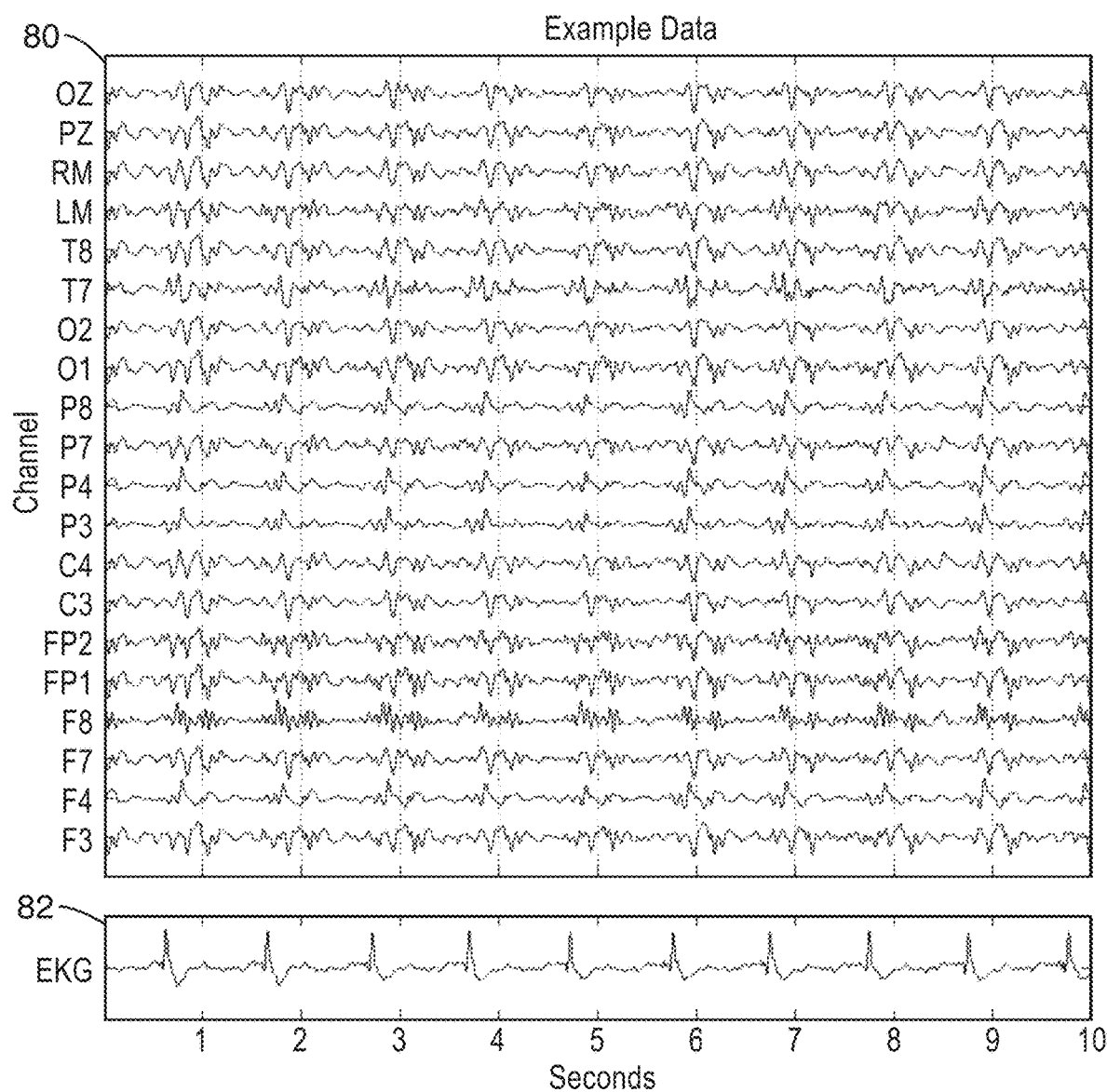
FIG. 3 illustrates exemplary EEG and ECG graphs, and demonstrates the extent to which BCG contaminates the EEG signals.

Second, current art assumes that the timing of an event in one channel is the same for all channels, which is also not the case. There time course of the flow of blood as it travels through the vasculature in the head is dispersed. Thus, there should be similar time dispersion of how the artifact propagates though the head (see FIG. 3, showing the various channels for each probe in the EEG graph 80 and ECG recording 82). The nature of how the two are related results from multiple components and causes noted above.

Third, the ECG recording system itself can act as a source of electronic noise both to the EEG and MRI instruments, leading to degraded recordings in both.

Fourth, the timing of the EEG and ECG recordings will be inexact if the clocks in the two recording devices are not locked precisely to one another. A common cause of this is error is that the EEG and ECG are recorded and digitized on separate instruments.

Fifth is the issue of attaching the ECG electrodes, the incorrect placement of which will lead to poor quality in the ECG recording. ECG electrode placement can be technically challenging due to variations in human anatomy from factors such as gender, size and weight.

Sixth, recording of the ECG during magnetic resonance imaging is subject to large contaminations from the MRI scanner. These contaminations result frequently in corruption of the ECG signal and inaccurate extraction of timing signals from the ECG.

Figure 1:
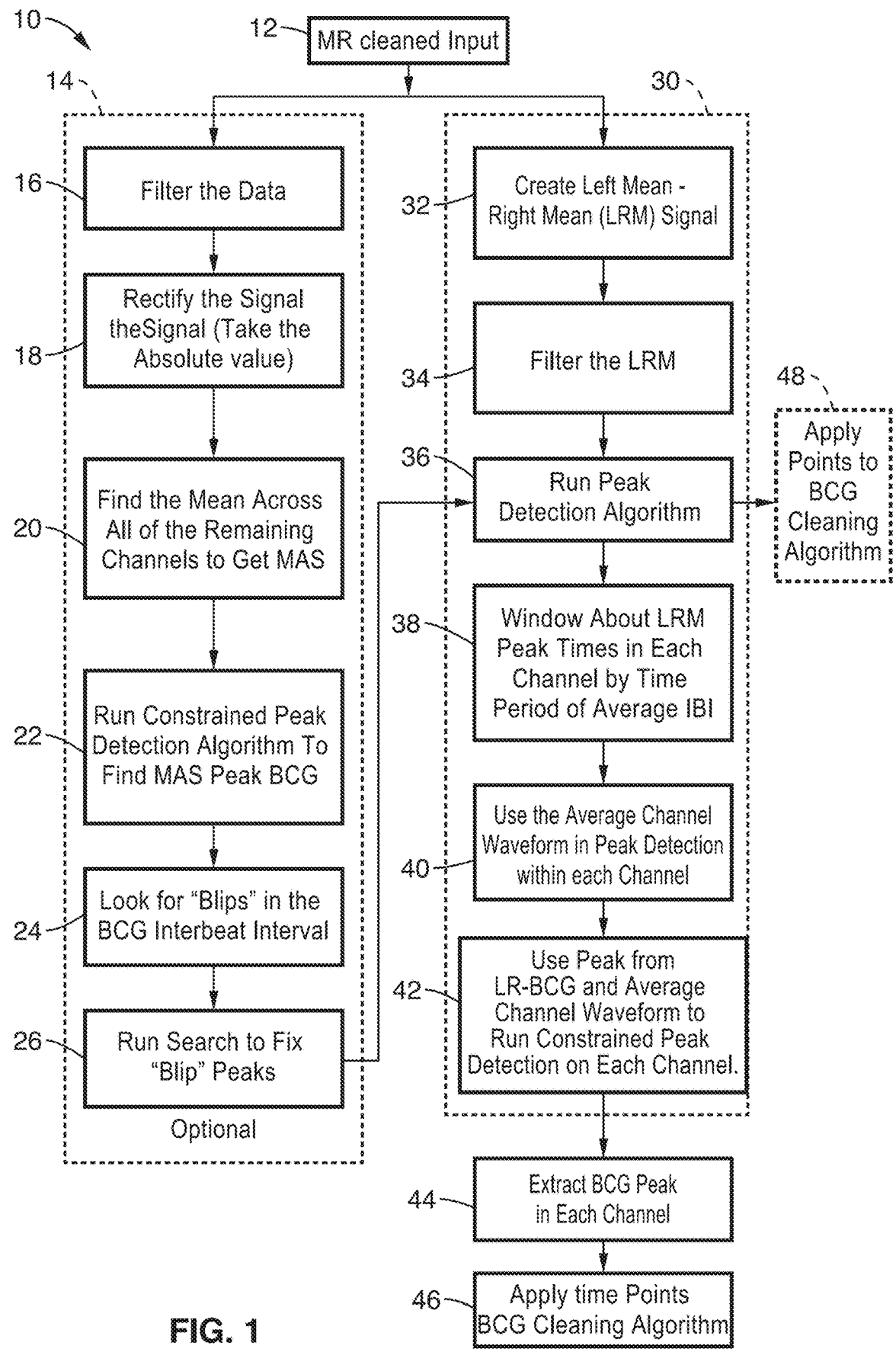
FIG. 1 illustrates an exemplary flow diagram of a method to extract cardiac timing from an electroencephalographic recording in accordance with the present description.

FIG. 1 shows an exemplary flow diagram of a method 10 for extracting cardiac timing from electroencephalograph data and in particular, ballistocardiographs. As mentioned above, the ballistocardiogram artifact (BCG) is the largest contaminate in the combined EEG-MRI recordings, FIG. 2.

In a preferred embodiment, method 10 may be implemented as a self-contained module of encoded instructions as part of application software 54 shown in FIG. 1. EEG is data 12 is passed in, and the cardiac timing 44 is passed out.

Initially, the MR-artifact cleaned data 12 is input into two separate pipelines 14, 30 for processing. Cardiac timing is extracted from both pipelines, and used as one of the several layers of built-in automatic error checking and correction. Using the two separate pipelines 14, 30 makes it possible to cross validate the timing measures. The first pipeline 14 provides a robust signal with regards to the BCG, however, the timing is not locked perfectly to the ECG. The second pipeline 30 provides a mechanically locked signal with respect to the ECG but, as it draws on fewer EEG channels, the signal to noise ratio is not as large. While it is preferential to have a multi-pipeline approach as described above and to cross-reference signals from each pipeline, it is appreciated that the first pipeline 14 is optional, and the method 10 may be employed with use of the second pipeline 30 individually.

In the first pipeline 14, the robust signal as well as optional mean of the absolute (MAS) signal is created. Channels are determined to be acceptable either through impedance measurements made by the EEG system or by analyzing the statistical properties of the signal within a channel. The MAS signal is then constructed by taking the mean of the absolute signal within channel across channels deemed acceptable. As shown in FIG. 1, the cleaned input 12 is first filtered (e.g. via a high order band pass filter) at step 16 and then rectified (i.e. the absolute value is taken) at step 18. It is understood that the MAS can be constructed from filtered and unfiltered versions of the EEG signals, and thus filtering step 16 is optional. The mean signal is then extracted at step 20 across all channels deemed to have impedance measured within an acceptable range to get the mean of the absolute signal (MAS).

At step 22, the MAS is then run through a constrained peak detection algorithm to find the MAS BCG peak. In one embodiment, constraints are applied to the peak detection algorithm to find the "R-Wave" equivalent peak. The applied constraints are based upon the nature of the data as well as physiological limits: the signal voltage range, as well as a reasonable range for heart rates in a supine position based upon subject age, are used to set a target range for detection. The first constraint speeds the calculations by helping to narrow down the search range, while the second forces the detected points to lie within a physically realistic range, thereby rejecting outliers and artifacts.

The method of step 22 can be steered astray by subject motion artifacts such as eye blinks, head or jaw movement. To counteract this problem, the first stage of error checking and correction is applied at step 22 by examining the rate of change of the heartbeat timing, the inter-beat interval (IBI). At step 24, the method looks for "blips" (e.g. anomalies) in the BCG "R-R" or interbeat interval, and then runs a search to fix "blip" peaks at step 26. The automatic error checking and correction algorithm is shown in more detail in FIG. 7.

In the second pipeline 30, the time locked signal data, which is the left mean-right mean (LRM), is reduced to channels corresponding to electrodes 65 that lie in closest proximity to the facial arteries (see FIG. 4 and FIG. 5) at step 32 to create the LRM reference signal. The shaded electrodes 65 (e.g. electrodes $F_7$, $C_3$, $T_7$, $A_1$ for the left channel and $F_8$, $C_4$, $T_8$, and $A_2$ for the right channel) were chosen because they contain a large component of pulsatile motion artifact of scalp that arises from the blood flowing in arteries beneath them which is coupled mechanically to the heartbeat through the hydraulics of the circulatory system. It is understood that the electrode channels 65 chosen are not restricted to the ones displayed in FIG. 4 and FIG. 5, but rather can be any electrodes/channels in close proximity to vasculature. From this channel subset the LRM is constructed by taking the mean of the signals from left hemisphere's channels and subtracting it from the mean of the signals of the right hemisphere's channels at step 34, which may include further band-pass filtering.

Next, a peak detection algorithm with built-in error checking is applied at step 36 to find the "R-Wave" equivalent peak in the LRM signal. The peak detection algorithm 36 (which may be constrained) runs on the signal(s) from step 34, and with the optional addition inputs of the signal(s) from pipeline 14. For example, the peak detection algorithm may be primed with the timing of the MAS events from step 26. The constrained peak detection algorithm is shown in further detail with respect to FIG. 6.

One of two things can then happen with the time points/peaks of the LRM signal acquired at step 36. The first is they can be passed into searches within each EEG channel and a process similar to peak detection of the LRM pipeline is run, except for the peak detection algorithm is primed with the peak times of the LRM, as explained above. In an optional configuration, output 48 from the peak detection algorithm 36 may be processed to apply acquired time points to a BCG cleaning algorithm available in the art.

After this final validation, the LRM time points are passed into searches within each EEG channel, and a process similar to the LRM pipeline is run, except for the priming of the measured peak times of the LRM. At step 38, the acquired time points from step 36 are windowed by the time period of the average IBI (e.g. a heart rate of 60 BPM=1 sec window). At step 40, the Average Channel Waveform is used for peak detection in each channel.

At step 42, the peak detected from the LR-BCG in step 36 and the average channel waveform from step 40 are used to run constrained peak detection on each channel.

Once the timing locations for all of the artifacts have been detected, they are returned as the primary processing output in step 44, which extracts BCG peak data in each channel. This can then be fed into an artifact correction algorithm in step 46.

Figure 2:
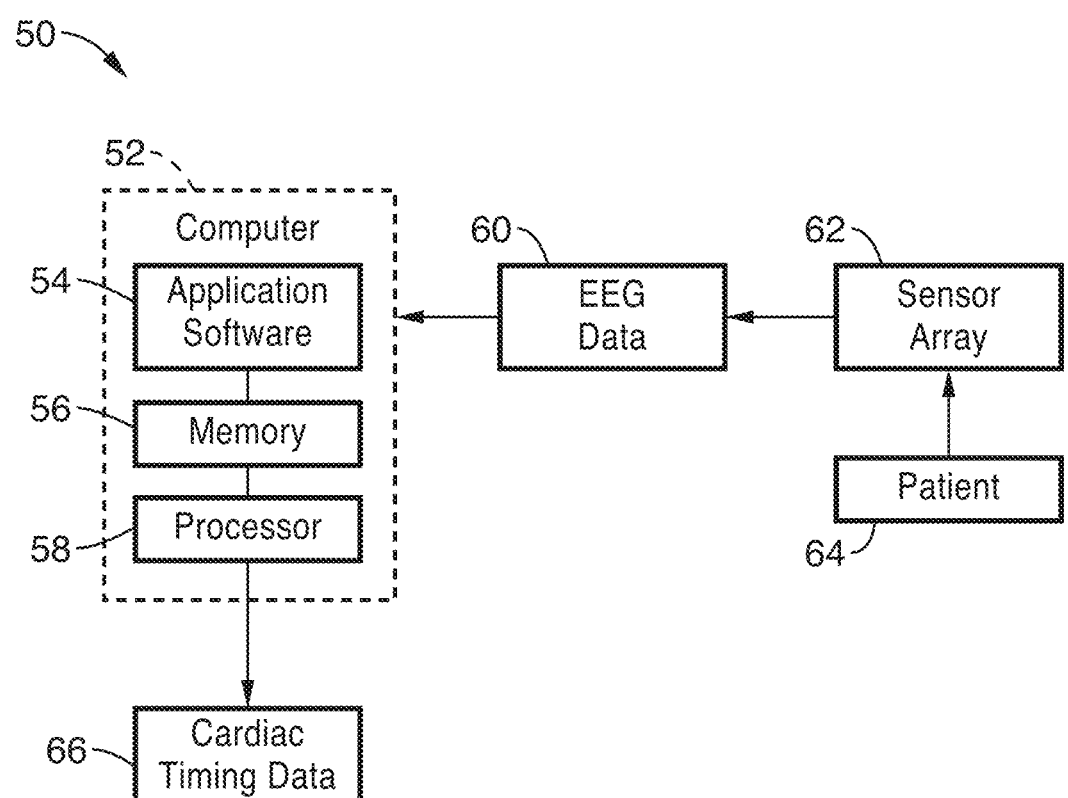
FIG. 2 is a schematic diagram of a system to extract cardiac timing from an electroencephalograph in accordance with the present description.

FIG. 2 is a schematic diagram of a system 50 for extracting cardiac timing from an electroencephalograph, and in particular, BCG. The system preferably includes a processing device, e.g. computer or server 52 having memory 56 for storing application software 54 having instructions configured for executing the methods of the present description (e.g. method 10 of FIG. 1) on processor 58. The computer 52 is configured to receive as input EEG data 60 (which may include MR cleaned EEG data 12 shown in FIG. 1) acquired from the patient 64 from EEG array 62, and outputs cardiac timing data 66 (e.g. extracted ECG peak equivalents from module 44 of FIG. 1).

FIG. 3 is a 10 second exemplary plot of selected electrodes of EEG data 80 recorded during an imaging procedure inside an MRI scanner, but after an MR gradient artifact cleaning algorithm has been applied. The EEG 80 and ECG 82 recording were made within a Siemens' Tim Trio 3T MRI during an echo planar imaging (EPI) sequence. The EEG and ECG recordings were made with Electrical Geodesics Incorporated's Net Amps 300 MRI compatible system. All electrodes referenced to Cz. Note the large deflections in the EEG 80 that arise from cardiovascular processes. It is clear from visual inspection that the ballistocardiogram (BCG) artifact has different peak onset times depending on the electrode location with respect to the head and facial arteries.

Figure 4:
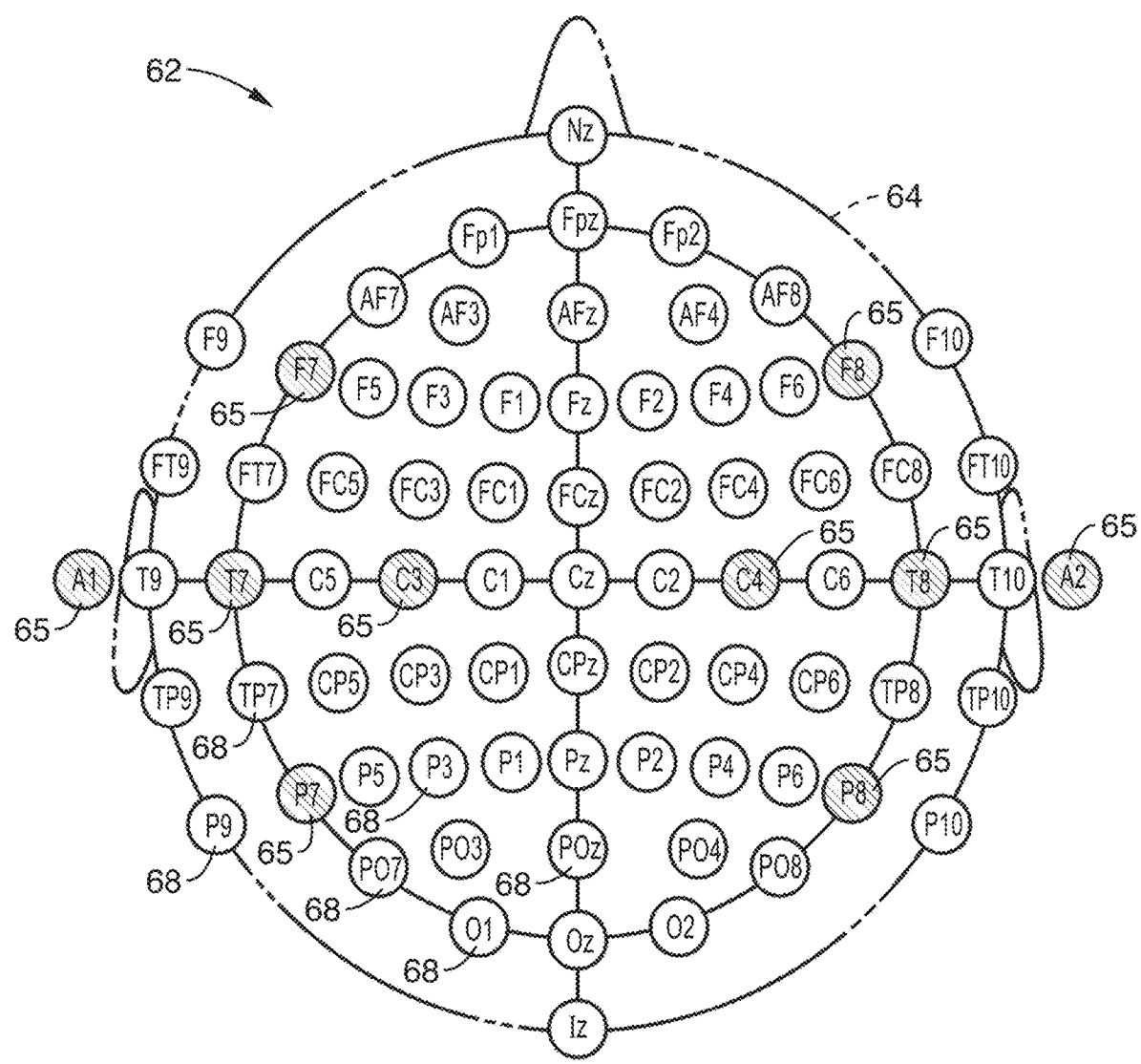
FIG. 4 shows a topographic view of the layout of an Extended 10-20 EEG system with an array of EEG electrodes disposed in relation to a subject.

FIG. 4 shows a topographic view of the layout of an Extended 10-20 EEG System 62 with an array of EEG electrodes 68 disposed in relation to patient 64. The shaded electrodes 65 are those used to generate the Left-Right Mean (LRM) EEG signal in step 32 of method 20. In the cases where electrodes A1 and A2 are not present, electrodes TP9 and TP10 or LM and RM respectively can be used in their place.

Figure 5:
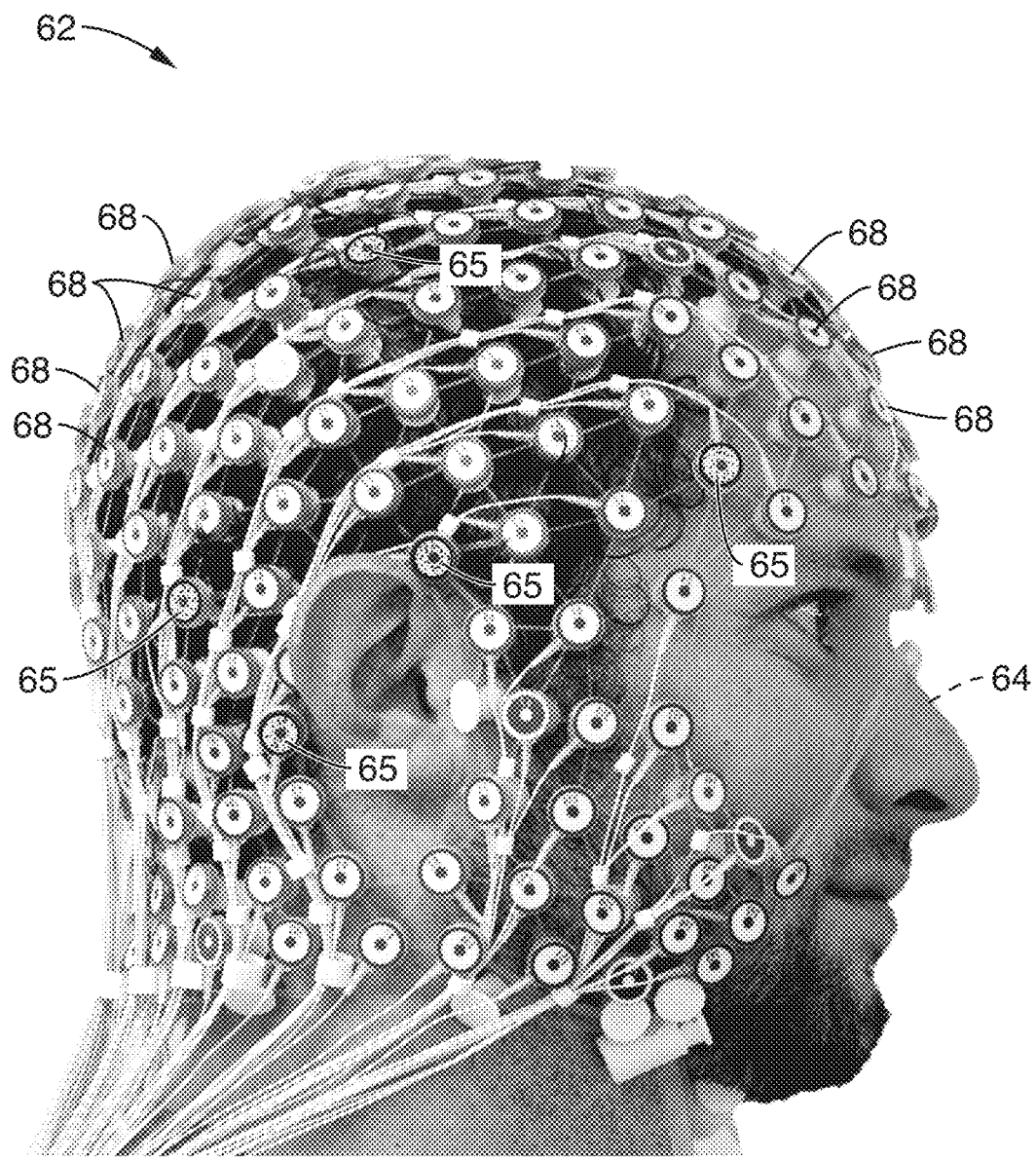
FIG. 5 shows a subject wearing an EEG electrode net configured for specified placement according to facial arteries of the subject.

FIG. 5 shows a subject wearing an Extended 10-20 EEG System 62. The left side 10-20 electrodes 65 corresponding to channels used to generate the L-R mean are shaded. The locations of the L-R mean generating electrodes 65 are positioned to coincide with the locations of the facial arteries (e.g. one or more of temporal, orbital, frontal branch, parietal branch, etc.)

Figure 6:
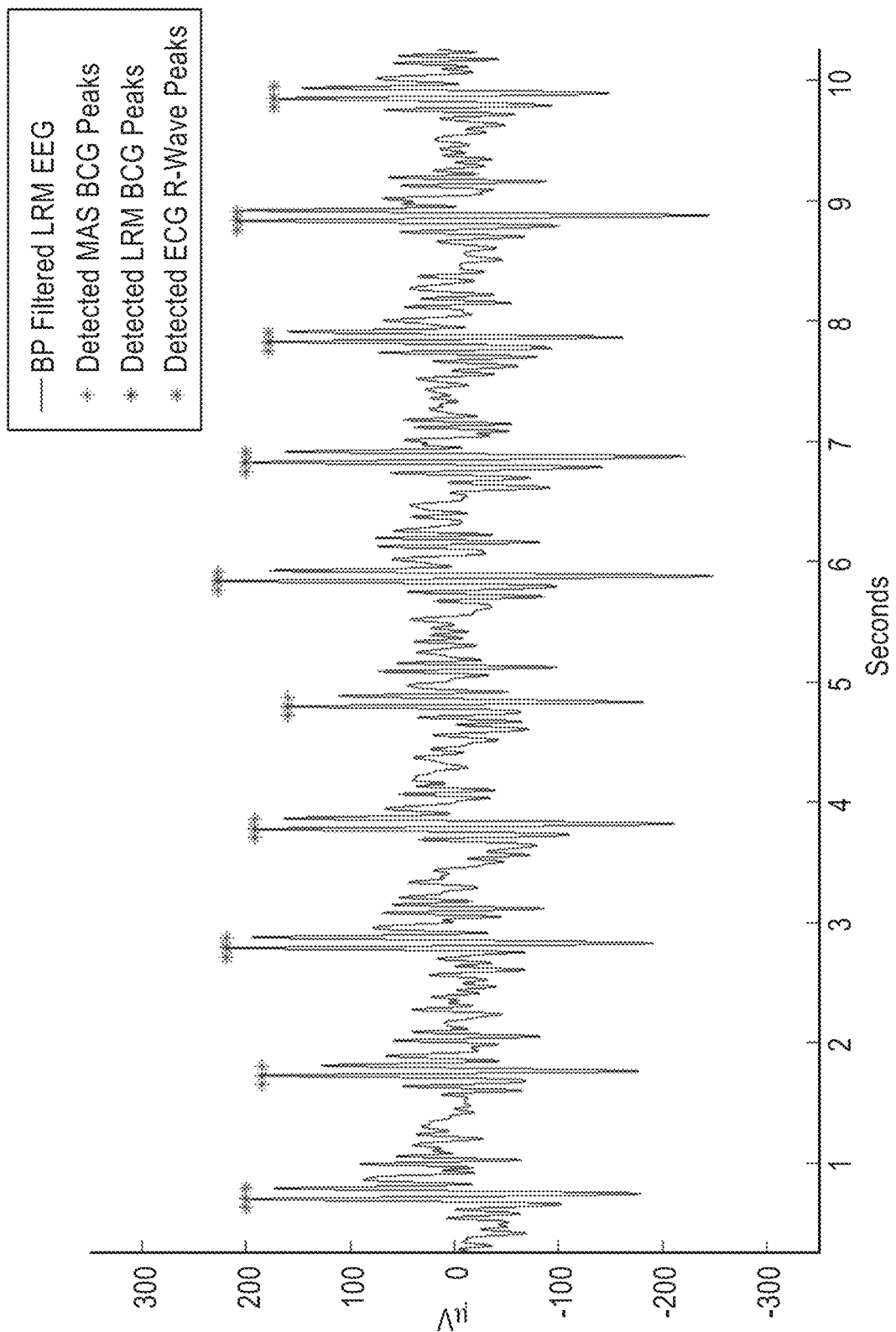
FIG. 6 shows a plot illustrating Left-Right Mean (LRM) and peak timing in accordance with the method of FIG. 1.

FIG. 6 shows a plot illustrating LRM and peak timing in accordance with method 10. A peak detection algorithm (e.g. step 36 in FIG. 1) is used to find the BCG events.

Figure 7A:
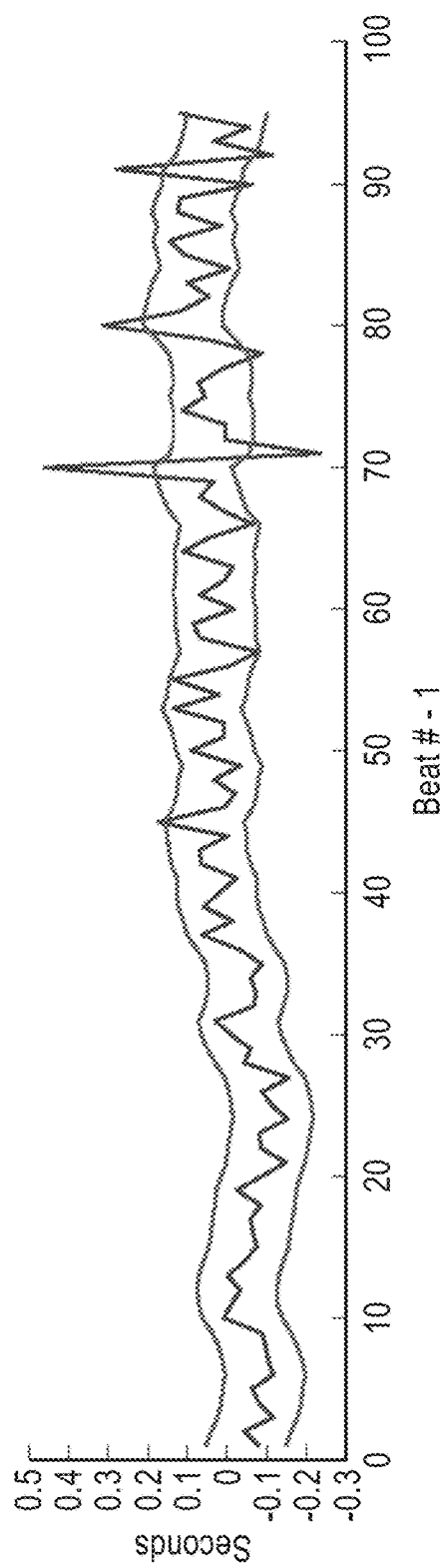
FIG. 7A and FIG. 7B are plots depicting inter-beat interval and fences in accordance with the method of FIG. 1.
Figure 7B:
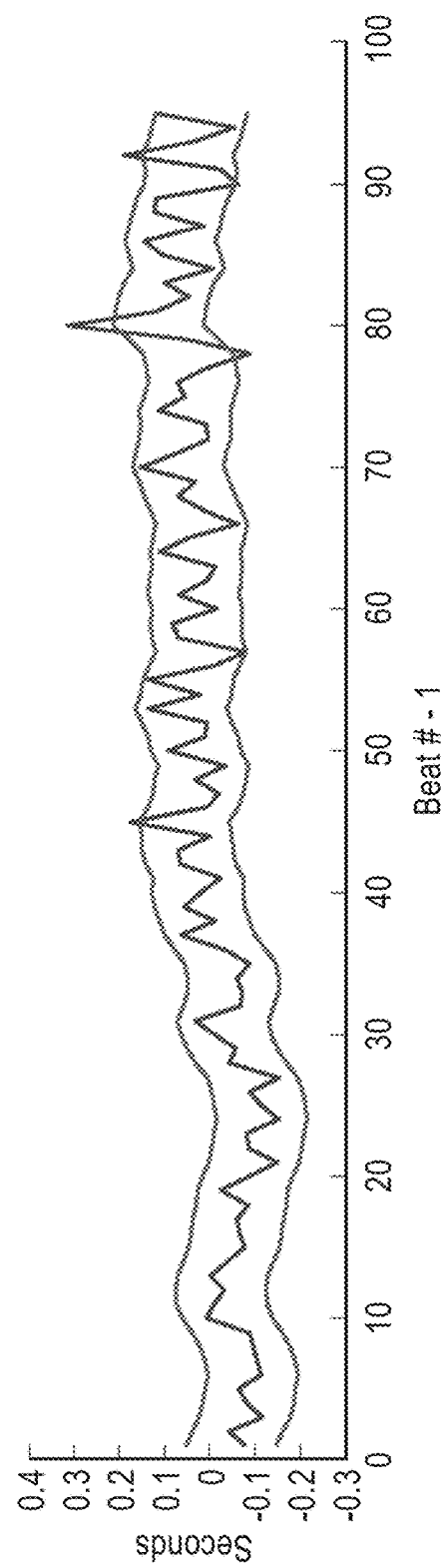

FIG. 7A and FIG. 7B are plots depicting one way automatic error checking can be implemented based upon the inter-beat interval and fences in accordance with the method 10 of FIG. 1. A zero-phase moving average filter on the detected inter-beat interval (IBI) is run to set fences so that incorrectly detected peaks can be determined and corrected automatically. Detected beats where the previous and following IBI's are outside the above determined fences, are deemed to be errors. A local search around the expected peak is run, and the peaks are corrected. In the plots of FIG. 7A the center line represents the difference from the mean heart rate and the outer lines represent the fences set based upon the zero phase moving average of the IBI. Notice that the periods in the plot of FIG. 7A, where there is double deviation from the moving average fences, are corrected for in the plot of 7B.

FIG. 8A through FIG. 8C are plots illustrating windowing about the various detected peaks for numerous EEG channels and for the ECG. In FIG. 8A, the EEG &ECG signals are windowed and averaged about the detected R-Wave Peak of the ECG. In FIG. 8B, the same is done, but the windowing is about the detected peak in the LRM signal. In FIG. 8C, the averages from FIG. 8A and FIG. 8B are aligned based upon the mean difference between the ECG R-wave peak and the LRM EEG peak and then subtracted from one another. The line 90 in each channel represents the difference and is a source of large potential error in estimating the BCG signal timing from the ECG.

Figure 9A:
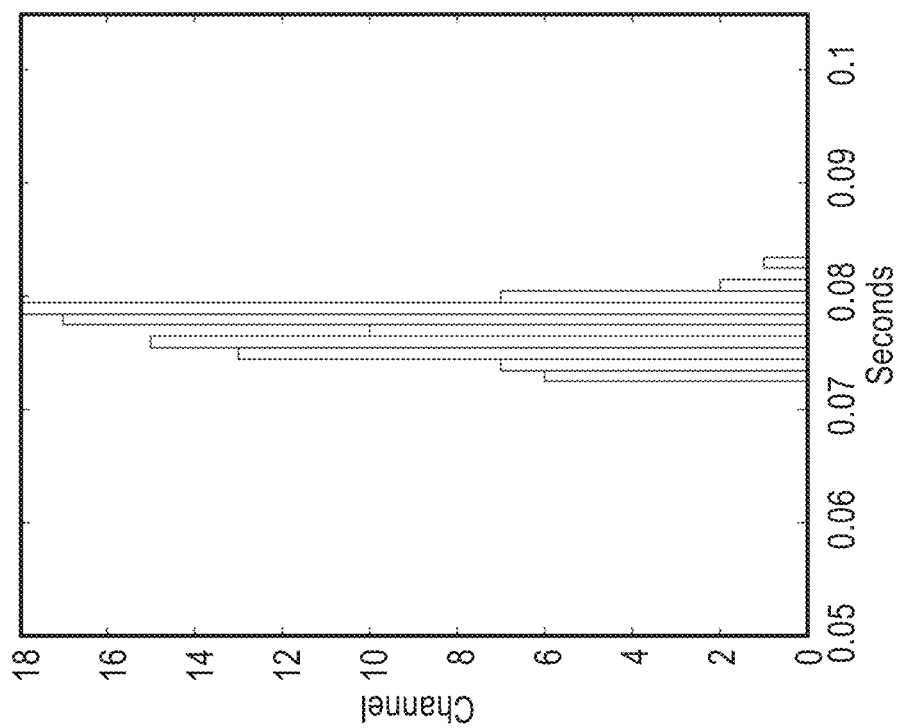
FIG. 9A and FIG. 9B are histogram plots showing differences between ECG and BCG timing.
Figure 9B:
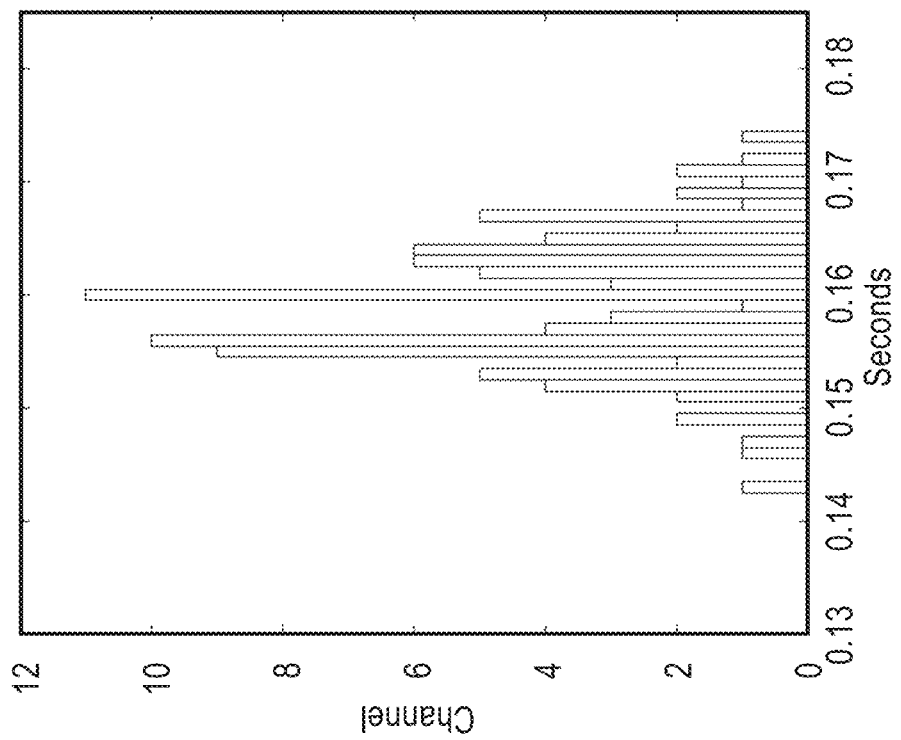

FIG. 9A and FIG. 9B are histogram plots showing differences in stability between ECG and MAS BCG timing and ECG and Left mean-Right Mean BCG timing. The histogram of FIG. 9A is the timing differences between the measured ECG R-wave peak and the respective peak in the MAS—representing current state-of-the-art in timing. The mean difference=0.159 sec, with standard deviation=0.0061 sec. The histogram of FIG. 9B reflects the timing difference between BCG and ECK peaks from LRM pipeline 30 of method 10 of the present description. The mean difference=0.077 sec, with standard deviation=0.0021 sec. As shown in FIG. 9A and FIG. 9B, the method of the present description shown in FIG. 9B illustrates much more consistent timing. Measurements were acquired from a study with a digital sampling frequency of 1 kHz; the observed standard deviation of ~2 msec is at the approximate theoretical limit of detection.

Embodiments of the present technology may be described with reference to flowchart illustrations of methods and systems according to embodiments of the technology, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

It will further be appreciated that the terms "programming" or "program executable" as used herein refer to one or more instructions that can be executed by a processor to perform a function as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors. It will further be appreciated that as used herein, that the terms processor, computer processor, central processing unit (CPU), and computer are used synonymously to denote a device capable of executing the instructions and communicating with input/output interfaces and/or peripheral devices.

From the description herein, it will be appreciated that that the present disclosure encompasses multiple embodiments which include, but are not limited to, the following:

1. A system for extracting cardiac timing from electroencephalograph (EEG) data: (a) an array of EEG electrodes configured to be positioned over at least a portion of a subject's head, wherein each electrode in the array of EEG electrodes is configured to generate EEG data on a dedicated channel; (b) a computer processor coupled to the array of EEG electrodes; and (c) a memory storing instructions executable on the computer processor, the instructions when executed by the computer processor performing steps comprising: (i) acquiring EEG data from the array of EEG electrodes; (ii) generating a reference signal from a selected portion of EEG channels, the selected portion of EEG channels corresponding to one or more electrodes in close proximity to one or more facial arteries of the subject, the reference signal being highly correlated to more facial arteries ballistocardiogram (BCG) artifact; and (iii) extracting cardiac timing data from the EEG data as a function of the generated reference signal.

2. The system of any preceding embodiment, wherein the cardiac timing comprises global BCG timing is extracted independently of accompanying ECG data acquired while acquiring the EEG data.

3. The system of any preceding embodiment, wherein the array of EEG electrodes comprises a subset of EEG electrodes specifically positioned to coincide with one or more facial arteries contributing to scalp-pulsation based BCG artifact.

4. The system of any preceding embodiment, wherein generating a reference signal from a selected portion of EEG channels comprises generating a Left-Right Mean difference (LRM) signal corresponding to a mean of left-side EEG electrodes of the selected portion of EEG channels subtracted from a mean of right-side EEG electrodes of the selected portion of EEG channels.

5. The system of any preceding embodiment, the instructions when executed by the computer processor further performing steps comprising: detecting a BCG peak from the LRM signal.

6. The system of any preceding embodiment, the instructions when executed by the computer processor further performing steps comprising: calculating a mean across all channels in the array of EEG electrodes to generate a mean absolute signal (MAS); and cross-correlating the LRM signal with the MAS signal to extract a BCG peak either globally or within each channel.

7. The system of any preceding embodiment, wherein the data from the MAS signal is used to aid detection of the BCG peak in the LRM signal.

8. The system of any preceding embodiment, the instructions when executed by the computer processor further performing steps comprising: automatically checking and correcting for errors in BCG peak detection of the LRM signal as a function of inter-beat timing.

9. The system of any preceding embodiment, wherein automatically checking and correcting for errors in BCG peak detection within individual EEG channels comprises searching for an anomaly in a BCG interbeat interval of the MAS signal and correcting for said anomalies.

10. The system of any preceding embodiment, the instructions when executed by the computer processor further performing steps comprising: windowing about times of the BCG peak from the LRM signal by a time period of an average interbeat interval.

11. A method for extracting cardiac timing from electroencephalograph (EEG) data: acquiring EEG data from an array of EEG electrodes disposed around the head of a subject; generating a reference signal from a selected portion of EEG channels, the selected portion of EEG channels corresponding to one or more electrodes in close proximity to one or more facial arteries of the subject, the reference signal being highly correlated to one or more facial arteries ballistocardiogram (BCG) artifacts; and extracting cardiac timing data from the EEG data as a function of the generated reference signal.

12. The method of any preceding embodiment, wherein the cardiac timing comprises global BCG timing is extracted independently of accompanying ECG data acquired while acquiring the EEG data.

13. The method of any preceding embodiment, wherein prior to acquiring EEG data, the array of EEG electrodes is positioned on the subject's head such that a subset of EEG electrodes are specifically positioned to coincide with one or more facial arteries contributing to scalp-pulsation based BCG artifacts.

14. The method of any preceding embodiment, wherein generating a reference signal from a selected portion of EEG channels comprises generating a Left-Right Mean difference (LRM) signal corresponding to a mean of left-side EEG electrodes of the selected portion of EEG channels subtracted from a mean of right-side EEG electrodes of the selected portion of EEG channels.

15. The method of any preceding embodiment, the method further comprising the step of: detecting a BCG peak from the LRM signal.

16. The method of any preceding embodiment, the method further comprising the steps of: calculating a mean across all channels in the array of EEG electrodes to generate a mean absolute signal (MAS); and cross-correlating the LRM signal with the MAS signal to extract a BCG peak either globally or within each channel.

17. The method of any preceding embodiment: wherein the data from the MAS signal is used to aid detection of the BCG peak in the LRM signal.

18. The method of any preceding embodiment, the method further comprising the step of: automatically checking and correcting for errors in BCG peak detection of the LRM signal as a function of inter-beat timing.

19. The method of any preceding embodiment, wherein automatically checking and correcting for errors in BCG peak detection within individual EEG channels comprises searching for an anomaly in a BCG interbeat interval of the MAS signal and correcting for said anomalies.

20. The method of any preceding embodiment, the method further comprising the step of: windowing about times of the BCG peak from the LRM signal by a time period of an average interbeat interval.

21. A system for extracting cardiac timing from electroencephalograph (EEG) data, the system comprising: (a) an array of EEG electrodes configured to be positioned over at least a portion of a subject's head, wherein each electrode in the array of EEG electrodes is configured to generate EEG data on a dedicated channel; (b) a computer processor coupled to the array of EEG electrodes; and (c) memory storing instructions executable on the processor, the instructions, when executed, performing the steps comprising: (i) acquiring EEG data from the array of EEG electrodes; (ii) generating a reference signal from a selected portion of EEG channels, the selected portion of EEG channels corresponding to one or more electrodes in close proximity to one or more facial arteries of the subject, the reference signal being highly correlated to one or more facial arteries ballistocardiogram (BCG) artifacts; (iii) calculating a mean across all channels in the array of EEG electrodes to generate a mean absolute signal (MAS); (iv) extracting BCG timing data from all channels in the array of EEG electrodes as a function of the generated reference signal.

22. The system of any preceding embodiment, wherein the array of EEG electrodes comprises a subset of EEG electrodes specifically positioned at or near facial vasculature contributing to scalp-pulsation based BCG artifacts.

23. The system of any preceding embodiment, wherein generating a reference signal from a selected portion of EEG channels comprises generating a Left-Right Mean difference (LRM) signal corresponding to a mean of left-side EEG electrodes of the selected portion of EEG channels subtracted from a mean of right-side EEG electrodes of the selected portion of EEG channels.

24. The system of any preceding embodiment, the instructions when executed by the computer processor further performing steps comprising: cross-correlating the LRM signal with the MAS signal to extract one or more BCG peaks in each channel; and extracting the BCG timing data independently of accompanying ECG data acquired while acquiring the EEG data.

25. The system of any preceding embodiment, wherein the data from the MAS signal is used to aid detection of the BCG peak in the LRM signal.

26. The system of any preceding embodiment, the instructions further comprising the step of: automatically checking and correcting for errors in BCG peak detection of the LRM signal as a function of inter-beat timing.

27. The system of any preceding embodiment, wherein automatically checking and correcting for errors in BCG peak detection within individual EEG channels comprises searching for an anomaly in a BCG interbeat interval of the MAS signal and correcting for said anomalies.

28. The system of any preceding embodiment, the instructions when executed by the computer processor further performing steps comprising: windowing about times of the BCG peak from the LRM signal by a time period of an average interbeat interval.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A system for extracting cardiac timing from electroencephalograph (EEG) data:
   (a) an array of EEG electrodes configured to be positioned over at least a portion of a subject's head, wherein each electrode in the array of EEG electrodes is configured to generate EEG data on a dedicated channel;
   (b) a computer processor coupled to the array of EEG electrodes; and
   (c) a memory storing instructions executable on the computer processor, the instructions when executed by the computer processor performing steps comprising:
      (i) acquiring EEG data from the array of EEG electrodes;
      (ii) determining a selected portion of EEG channels corresponding to one or more electrodes in close proximity to one or more facial arteries of the subject;
      (iii) generating a reference signal from the selected portion of EEG channels correlated to ballistocardiogram (BCG) artifacts from the one or more facial arteries; and
      (iv) extracting cardiac timing data from the EEG data as a function of the generated reference signal.

2. A system as recited in claim 1, wherein the cardiac timing comprises global BCG timing that is extracted independently of accompanying ECG data acquired while acquiring the EEG data.

3. A system as recited in claim 1, wherein the array of EEG electrodes comprises a subset of EEG electrodes specifically positioned to coincide with one or more facial arteries contributing to scalp-pulsation based BCG artifact.

4. A system as recited in claim 1, wherein generating the reference signal from the selected portion of EEG channels comprises generating a Left-Right Mean difference (LRM) signal corresponding to a mean of left-side EEG electrodes of the selected portion of EEG channels subtracted from a mean of right-side EEG electrodes of the selected portion of EEG channels.

5. A system as recited in claim 4, the instructions when executed by the computer processor further performing steps comprising:
   detecting a BCG peak from the LRM signal.

6. A system as recited in claim 5, the instructions when executed by the computer processor further performing steps comprising:
   calculating a mean across all channels in the array of EEG electrodes to generate a mean absolute signal (MAS); and
   cross-correlating the LRM signal with the MAS signal to extract the BCG peak either globally or within each channel.

7. A system as recited in claim 6, wherein the data from the MAS signal is used to aid detection of the BCG peak in the LRM signal.

8. A system as recited in claim 6, the instructions when executed by the computer processor further performing steps comprising:
   automatically checking and correcting for errors in BCG peak detection of the LRM signal as a function of inter-beat timing.

9. A system as recited in claim 8, wherein automatically checking and correcting for errors in BCG peak detection within individual EEG channels comprises searching for an anomaly in a BCG interbeat interval of the MAS signal and correcting for said anomalies.

10. A system as recited in claim 5, the instructions when executed by the computer processor further performing steps comprising:
    windowing about times of the BCG peak from the LRM signal by a time period of an average interbeat interval.

* * * * *